US012311159B2

(12) United States Patent
Elibol et al.

(10) Patent No.: US 12,311,159 B2
(45) Date of Patent: May 27, 2025

(54) VACUUM ASSISTED SUTURELESS INFLOW CANNULA AND RING IMPLANTATION OF VENTRICULAR ASSIST DEVICES

(71) Applicant: Ahmet Elibol, Istanbul (TR)

(72) Inventors: Ahmet Elibol, Istanbul (TR); Hamdi Yigit Elibol, Istanbul (TR)

(73) Assignee: Ahmet Elibol, Istanbul (TR)

( * ) Notice: Subject to any disclaimer, the term of this patent is extended or adjusted under 35 U.S.C. 154(b) by 372 days.

(21) Appl. No.: 17/789,791

(22) PCT Filed: Dec. 7, 2020

(86) PCT No.: PCT/TR2020/051248
§ 371 (c)(1),
(2) Date: Jun. 29, 2022

(87) PCT Pub. No.: WO2021/137805
PCT Pub. Date: Jul. 8, 2021

(65) Prior Publication Data
US 2023/0044242 A1 Feb. 9, 2023

(30) Foreign Application Priority Data

Dec. 31, 2019 (TR) .................................. 201923195

(51) Int. Cl.
*A61M 60/00* (2021.01)
*A61M 60/148* (2021.01)
*A61M 60/178* (2021.01)
*A61M 60/863* (2021.01)

(52) U.S. Cl.
CPC ........ *A61M 60/178* (2021.01); *A61M 60/148* (2021.01); *A61M 60/863* (2021.01)

(58) Field of Classification Search
CPC .............. A61M 60/178; A61M 60/148; A61M 60/861–863
See application file for complete search history.

(56) References Cited

U.S. PATENT DOCUMENTS

| 9,125,648 | B2 * | 9/2015 | Hoarau | A61B 17/00 |
| 10,518,012 | B2 * | 12/2019 | Jimenez | A61M 60/216 |
| 2007/0265643 | A1 * | 11/2007 | Beane | A61F 2/064 |
| | | | | 606/153 |
| 2008/0009891 | A1 * | 1/2008 | Cohn | A61M 60/216 |
| | | | | 606/170 |
| 2012/0330122 | A1 * | 12/2012 | Ji | A61B 5/283 |
| | | | | 600/375 |
| 2018/0243488 | A1 * | 8/2018 | Callaway | A61M 60/857 |
| 2022/0016412 | A1 * | 1/2022 | Bourquin | A61M 60/81 |
| 2022/0296874 | A1 * | 9/2022 | Tsui | A61M 60/31 |

FOREIGN PATENT DOCUMENTS

| KR | 20170134043 A | 12/2017 |
| RU | 2189171 C2 | 9/2002 |

* cited by examiner

*Primary Examiner* — Eric D. Bertram
(74) *Attorney, Agent, or Firm* — Bayramoglu Law Offices LLC

(57) ABSTRACT

A ventricular assist device includes a fixation ring set and an inflow cannula designed in a suitable manner to left ventricle diameters and average heart dimensions for an adult woman and an adult man, wherein a surgical suture is not used in the ventricular assist device to provide an implantation facilitation and controlling of bleeding sites.

12 Claims, 9 Drawing Sheets

VACUUM ASSISTED SUTURELESS INFLOW CANNULA AND RING IMPLANTATION OF VENTRICULAR ASSIST DEVICES

CROSS REFERENCE TO THE RELATED APPLICATIONS

This application is the national stage entry of International Application No. PCT/TR2020/051248, filed on Dec. 7, 2020, which is based upon and claims priority to Turkish Patent Application No. 2019/23195 filed on Dec. 31, 2019, the entire contents of which are incorporated herein by reference.

TECHNICAL FIELD

The present invention relates to vacuum-assisted easy implantation of inflow cannula and ring of ventricular assist devices and configuring the implantation procedure which provides controlling of all bleeding sites.

The present invention moreover relates to a ventricular assist device comprising inflow cannula and fixation ring set designed in a compliant manner to the average heart dimensions for adult woman and man and to the left ventricle and where surgical sewing is not used and which provides implantation facilitation and control of all bleeding sites.

BACKGROUND

Heart failure is a growing public health problem associated with increased rates of the diseases (morbidity) and deaths (mortality) in population. Despite major advances in the management of acute and chronic end stage heart failure, the prevalence of heart failure increases due to the lack of donor organs. In USA, nearly 6 million patients are diagnosed with heart failure and this number is expected to increase. Optimal medical therapy continues to be one of the cornerstones of heart failure management, however, ventricular assist device-based (hereafter it will be mentioned as VAD) therapies have been shown to contribute to reduction in morbidity and mortality.

The ability to support or relapse the failing heart is one of the most important scientific inventions. One of the most important devices which provide heart transplantation and mechanical circulation support is the left ventricular assist device (LVAD).

As heart failure becomes more prevalent each year, LVAD usage and the number of cardio-pulmonary bypass (CPB) procedures are increasing. The treatment of end stage heart failure by means of LVADs has become a standard in cardiac surgery. Yet, technique for its surgical implantation of LVADs has not yet become standardized and differs from center to center.

In the known state of the art, the left ventricular assist device (LVAD) has an inflow cannula and an outflow cannula. The blood, which comes from the left ventricle by means of the inflow cannula, is pumped to the aorta by means of the outflow cannula. The inflow cannula is placed to the heart chamber, named as left ventricle, through the window formed by removing a cylindrical muscle tissue from the heart apex. With the help of devices named as coring borer, the cylindrical muscle tissue removed from the heart apex is defined as 'core myocardium.

In the art, among the steps of placing inflow cannula to the left ventricle, there are the processes of fixation of the inflow cannula to the heart muscle by means of surgical sutures, removal of the core myocardium, and engagement of the inflow cannula to the cannula ring. The fixed position of the inflow cannula at the heart apex is realized by means of the inflow cannula ring. Since this ring is fixed to the heart muscle (myocardium) with surgical sutures, it is called "sewing ring" in the literature.

In cardiac surgeries, although much smaller and less traumatic devices are produced and used, it is considered that focusing on the interaction between the device and the cardiovascular system is insufficient for the related technical field for the studies particularly related to the cannulation method.

Several steps of the implantation method remain unstandardized. The method used to suture the sewing ring to the myocardium was found to differ from center to center. Based on the devices and the surgical team, the insertion and fixation of the LVAD can vary. The surgical procedures and cannula design could influence the postoperative outcomes of the patient, particularly in respect to postoperative bleeding from the cannulation site.

Post-operative bleeding is a particularly significant problem during the acute phase of the mechanical circulatory support, occurring at suture lines and cannulation sites and can be difficult to localize. Other methods to prevent bleeding include minimizing time for CPB and surgical dissection and attaching felt reinforcements in areas of friable tissue. Previous studies have shown up to 76% of the patients experience excessive bleeding in the acute phase following LVAD implantation, with as many as 60% requiring operative intervention.

Several suture techniques, especially transmural stitching without back stitch, which are used for fixation of inflow and outflow cannula may result in bleeding around suture sites, thrombus around the cannula, and reduced end-organ perfusion.

It has been shown that the incidence of thrombotic events is much lower than bleeding events. Bleeding is one of the most common complications observed during VAD support and is a major contributing factor for operative mortality following LVAD implantation.

As a result, because of the problems mentioned above, an improvement is required in the related technical field.

SUMMARY

The present invention relates to a ventricular assist device, for eliminating the disadvantages mentioned above and for bringing new advantages to the related technical field.

An object of the present invention is to provide a ventricular assist device placed without using surgical suture.

An object of the present invention is to provide a ventricular assist device which provides controlling all bleeding sites.

An object of the present invention is to provide a ventricular assist device with vacuum assist which facilitates implantation.

An object of the present invention is to provide a ventricular assist device comprising inflow cannula and fixation ring set designed in a compliant manner to the adult woman and man left ventricle diameters.

In order to realize the abovementioned objects and the objects which are to be deducted from the detailed description below, the present invention relates to a ventricular assist device. Accordingly, the subject matter ventricular assist device comprises:

an inflow cannula placed into the left ventricle and which provides transferring of the blood, coming from this left ventricle, to the pump and which is made of metal;

a fixation ring which is locked to the inflow cannula and which provides fixation of the device at the heart apex;

a vacuum fixer which provides fixation by vacuuming the fixation ring, connected thereto, by means of the effect of negative pressure applied therein;

a core myocardium borer which cuts the heart muscle in a cylindrical manner through the heart apex and which removes the core myocardium; and a pump which provides increasing of the amount of blood circulating in the body when the core myocardium borer and one of the natural pumps do not operate in a firm manner.

By means of this, a ventricular assist device is obtained where surgical suture is not used and which facilitates implantation.

In a possible embodiment of the present invention, said inflow cannula comprises:

at least one fixation ring pin housing which is engaged with the fixation ring pins and which provides locking of the pump and the inflow cannula;

at least one pump pin housing engaged to the pump pins and which provides locking of the pump and the inflow cannula;

at least one fixation wing screw housing which provides fixation of the fixation wing screws to the inflow cannula;

at least one flat sealed rubber ring which fills the thin layer gap between the pump and the inflow cannula contact surfaces and which prevents probable blood leakage through this gap; and a round sealed rubber ring which fills the thin layer gap between the fixation ring and the inflow cannula contact surfaces and which prevents probable blood leakage through this gap.

In a possible embodiment of the present invention, said flat sealed rubber ring is made of bio-compliant silicon material. By means of this, a ventricular assist device is obtained which does not have a toxic effect and comprising fixation ring set and inflow cannula designed in a suitable manner to the left ventricle diameters and where surgical suture is not used and which provides implantation facilitation and which provides controlling of all bleeding sites.

In a possible embodiment of the present invention, said round sealed rubber ring is made of bio-compliant silicon material. By means of this, a ventricular assist device is obtained which does not have a toxic effect and comprising fixation ring set and inflow cannula designed in a suitable manner to the left ventricle diameters and where surgical suture is not used and which provides implantation facilitation and which provides controlling of all bleeding sites.

In a possible embodiment of the present invention, said fixation ring comprises:

at least one fixation wing as the engagement mechanism which provides fixation of the fixation ring to the heart;

at least one fixation wing which provides fixation of the fixation ring at the heart apex;

at least one fixation wing shaft which provides connection of the fixation wing to the fixation ring;

at least one fixation wing screw which joins the inflow cannula to the fixation ring and which provides fixation thereof to the heart muscle;

at least one fixation wing nut, which provides the fixation wing and heart muscle to be pushed towards the inflow cannula by turning the said fixation wing nut clockwise and fixes the inflow cannula on the heart by closing the gap around the inflow cannula;

at least one fixation wing screw positioner which provides alignment with the screw housings provided on the inflow cannula;

at least one fixation wing screw positioner slider which provides the movements of the fixation wing screw positioners on the wings;

at least one fixation pad which completely covers the inlet holes formed by the fixation wing screws at the heart muscle and which forms a barrier for bleeding;

at least one fixation ring pin which engages with the fixation ring pin housings provided on the inflow cannula and which provides locking of the inflow cannula with the fixation ring; and at least one temporary fixation screw which provides temporary fixation of the fixation wings, where the wing vacuum fixers are fixed, to the heart muscle.

By means of this, fixation ring is locked with the inflow cannula and the ventricular assist device is fixed at the heart apex.

In a possible embodiment of the present invention, said vacuum fixer comprises:

a fixation ring vacuum tube which provides transfer of negative pressure to the vacuum fixer;

at least one wing vacuum fixer which provides fixation of the fixation wings on the heart surface;

a wing vacuum inlet which provides transfer of negative pressure to the wing vacuum fixer;

at least one wing vacuum connector which provides connection of the wing vacuum tubes to the wing vacuum inlets;

at least one wing vacuum tube which provides transfer of negative pressure to the wing vacuum fixers; and a wing main vacuum tube which provides transfer of negative pressure to the wing vacuum lines.

In a possible embodiment of the present invention, said fixation ring vacuum tube is made of cylindrical and hollow bio-compliant silicon which has stiffness such that it does not become depressed as a result of negative pressure.

In a possible embodiment of the present invention, said wing vacuum fixer is made of bio-compliant silicon.

In a possible embodiment of the present invention, said wing vacuum connector is made of stiff and bio-compliant hollow plastic.

In a possible embodiment of the present invention, said wing vacuum tube is made of plastic pipe which has stiffness such that it does not become depressed as a result of negative pressure.

In a possible embodiment of the present invention, said wing main vacuum tube is made of bio-compliant silicon which has stiffness such that it does not become depressed as a result of negative pressure.

In a possible embodiment of the present invention, said core myocardium borer comprises a core myocardium borer positioner which keeps the inflow cannula at an axis of 90 degrees and which provides the heart muscle to be cut and removed at fixed position.

In a possible embodiment of the present invention, said pump comprises at least one pump pin which provides engagement to the compressive windows provided at the inflow cannula and which provides the pump to be locked to the inflow cannula.

The present invention relates to a method for operation of the ventricular assist device for use in implantation facilitation and in controlling of all bleeding sites. Said implantation method comprises the process steps of:

i. Marking the heart by means of surgical marker pen for the selection of the area where the inflow cannula is to be placed;
ii. Contacting the fixation ring and the vacuum fixer, which are fixed together, to the heart apex such that the marked area stays at the center of the fixation ring;
iii. Fixing the fixation ring to the heart apex by means of vacuum effect by means of application of negative pressure to the ventricular assist device by the vacuum fixer;
iv. Holding the three wings, where no vacuum is applied, to the heart muscle by means of temporary fixation screws;
v. Engaging the borer positioner to the fixation ring pins provided on the fixation ring and locking thereof in clockwise direction;
vi. Passing the core myocardium borer through the borer positioner and cutting the marked heart muscle in a cylindrical manner and in an orthogonal position to the fixation ring;
vii. Eliminating the core myocardium borer and the borer positioner from the surgery medium and afterwards removing the cut heart core myocardium;
viii. Passing the inflow cannula through the fixation ring and advancing thereof into the left ventricle;
ix. Removing the wing vacuum fixers and passing the fixation wing screws through the fixation wing screw positioners by punching the heart muscle and screwing thereof to the wing screw housings provided in the inflow cannula;
x. Removing the temporary fixation screws and placing the fixation wing screws instead as mentioned in step ix;
xi. Turning the fixation wing nuts in the clockwise direction and compressing of the heart muscle by the wings around the inflow cannula;
xii. Engaging the pump, designed according to the inflow cannula, to the pump pin housings, provided in the inflow cannula, by means of pump pins and turning in the clockwise direction and providing locking.

In a possible embodiment of the present invention, in step (ii), said negative pressure value is 250 mmHg.

In a possible embodiment of the present invention, in step (ii), as negative pressure is applied, the fixation wings are fixed to the heart muscle by means of the wing vacuum fixers and temporary fixation screws.

REFERENCE NUMBERS

1 Ventricular Assist Device
  10 Inflow Cannula
    11 Fixation Ring Pin Housing
    12 Pump Pin Housing
    13 Wing Screw Housing
    14 Flat Sealed Rubber Ring
    15 Round Sealed Rubber Ring
      20 Fixation Ring
    21 Fixation Wing
    22 Fixation Wing Shaft
    23 Fixation Wing Screw
    24 Fixation Wing Nut
    25 Fixation Wing Screw Positioner
    26 Fixation Wing Screw Positioner Slider
    27 Fixation Wing Pad
    28 Fixation Ring Pin
    29 Temporary Fixation Screw
      30 Vacuum Fixer
    31 Fixation Ring Vacuum Tube
    32 Wing Vacuum Fixer
    33 Wing Vacuum Inlet
    34 Wing Vacuum Connector
    35 Wing Vacuum Tube
    36 Wing Main Vacuum Tube
      40 Core Myocardium Borer
    41 Borer Positioner
      50 Pump
    51 Pump Pin
      60 Outflow Cannula

DETAILED DESCRIPTION OF THE EMBODIMENTS

In this detailed description, the subject matter relates to a ventricular assist device (1) comprising fixation ring (20) set and inflow cannula (10) designed in a suitable manner to the left ventricle diameters and average heart dimensions for the adult woman and man, and where surgical suture is not used and which provides implantation facilitation and which provides controlling of all bleeding sites, and is explained with references to examples without forming any restrictive effect only in order to make the subject more understandable.

The subject matter ventricular assist device (1) functions as a mechanical pump. When one of the natural pumps (a ventricle) of the heart does not function regularly, a VAD (1) is used for increasing the amount of blood which circulates in the body. VAD implant provides living of pluralities of persons, who have severe level heart failure, in a more comfortable manner.

As known in the art, VAD (1) comprises a pump connected to the ventricle in the heart; an external control unit which is a small computer which monitors said pump; a transfer line cable which connects the pump to the control unit; and power supplies which operate the pump and the control unit.

Figure 1:
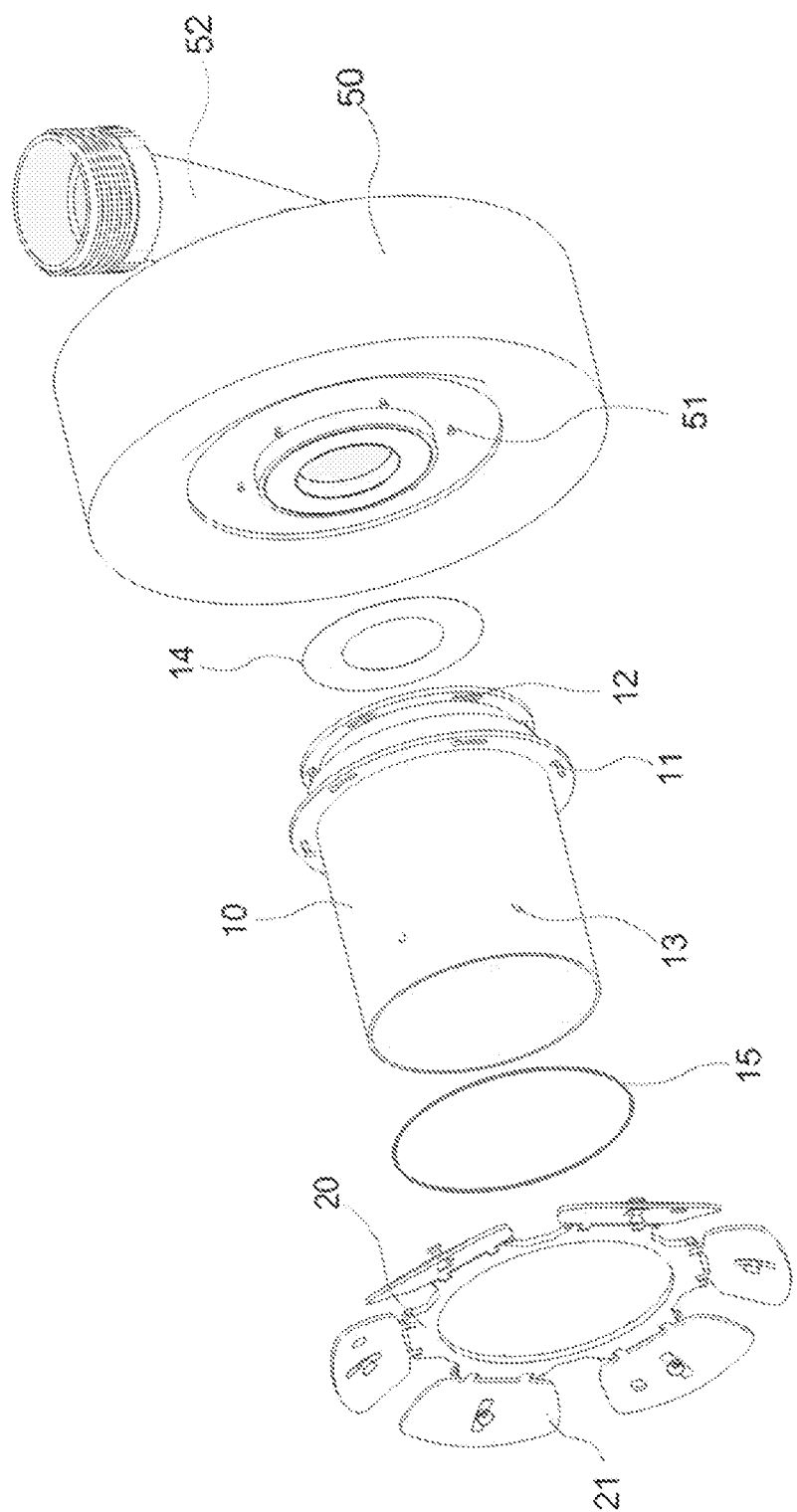
FIG. 1 is the view of the rubber rings, the pump, the inflow cannula and the fixation ring provided in the subject matter ventricular assist device.

The subject matter ventricular assist device (1) comprises an inflow cannula (10) placed into the left ventricle and which is made of metal and which provides transfer of the blood, coming from the left ventricle, to the pump (50). Said inflow cannula (10) has been designed for engagement with the pump (50) and has been produced with different diameters and sizes, and the possibility of selection and placement of the most suitable inflow cannula (10) to the left ventricle of the patient is presented by means of the set. As shown in FIG. 1, the inflow cannula (10) comprises engagement mechanisms with the pump (50).

As said engagement mechanisms on the inflow cannula (10), at least one fixation ring pin housing (11), at least one pump pin housing (12), at least one wing screw housing (13), a flat sealed rubber ring (14) and round sealed rubber ring (15) are used.

Said fixation ring pin housing (11) is engaged with the fixation ring pins (28) and provides locking of the pump (50) and the inflow cannula (10).

Said pump pin housing (12) is engaged with the pump pins (51) and provides locking of the pump (50) and the inflow cannula (10).

Figure 5:
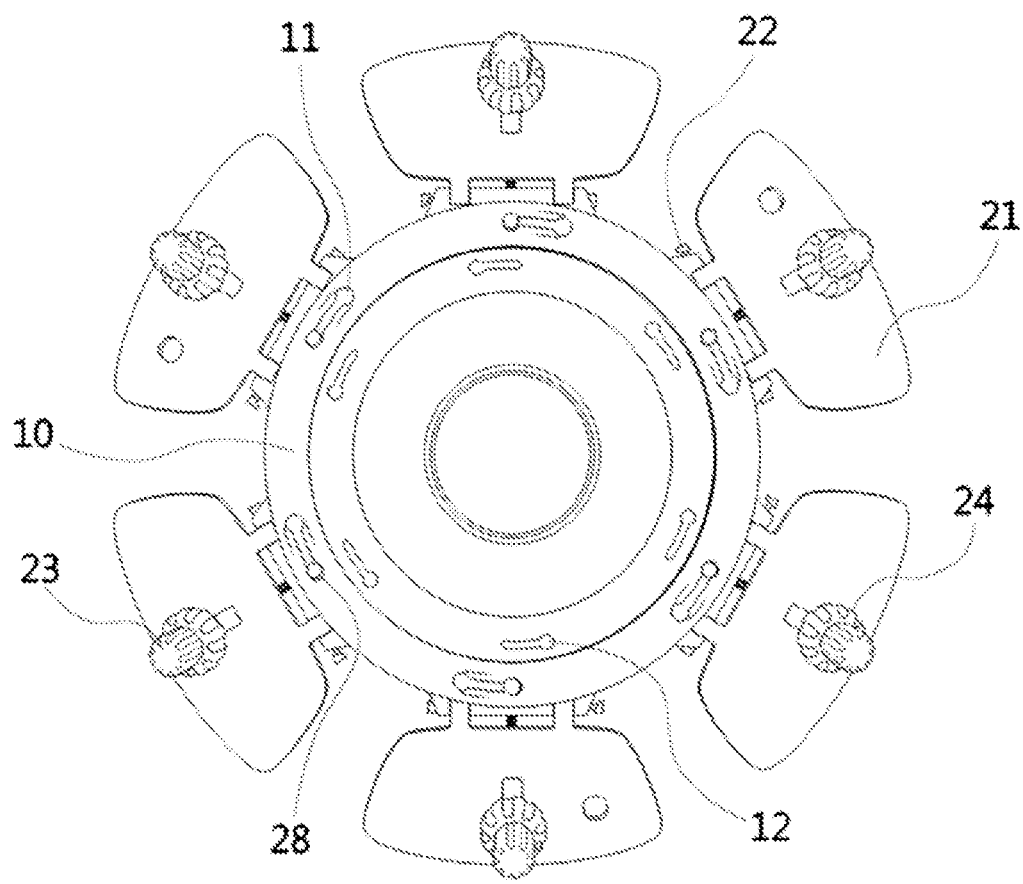
FIG. 5 is the top view where the inflow cannula and fixation ring, provided in the subject matter ventricular assist device, are engaged with the wing screw and nuts.

The fixation wing screw housing (13), shown in FIG. 5, provides fixation of the fixation wing screws (23) to the inflow cannula (10).

Said flat sealed rubber ring (14) fills the thin layer gap between the pump (50) and the inflow cannula (10) contact surfaces, and prevents probable blood leakage through this gap. The flat sealed rubber ring (14) is made of bio-compliant silicon material.

Said round sealed rubber ring (15) fills the thin layer gap between the fixation ring (20) and the inflow cannula (10) contact surfaces, and prevents probable blood leakage through this gap. The round sealed rubber ring (15) is made of bio-compliant silicon material.

The subject matter ventricular assist device (1) comprises a fixation ring (20) locked with the inflow cannula (10) and which provides the device to stay at the heart apex. Said fixation ring (20) comprises engagement mechanisms which provide fixation of the device and the heart.

Figure 2:
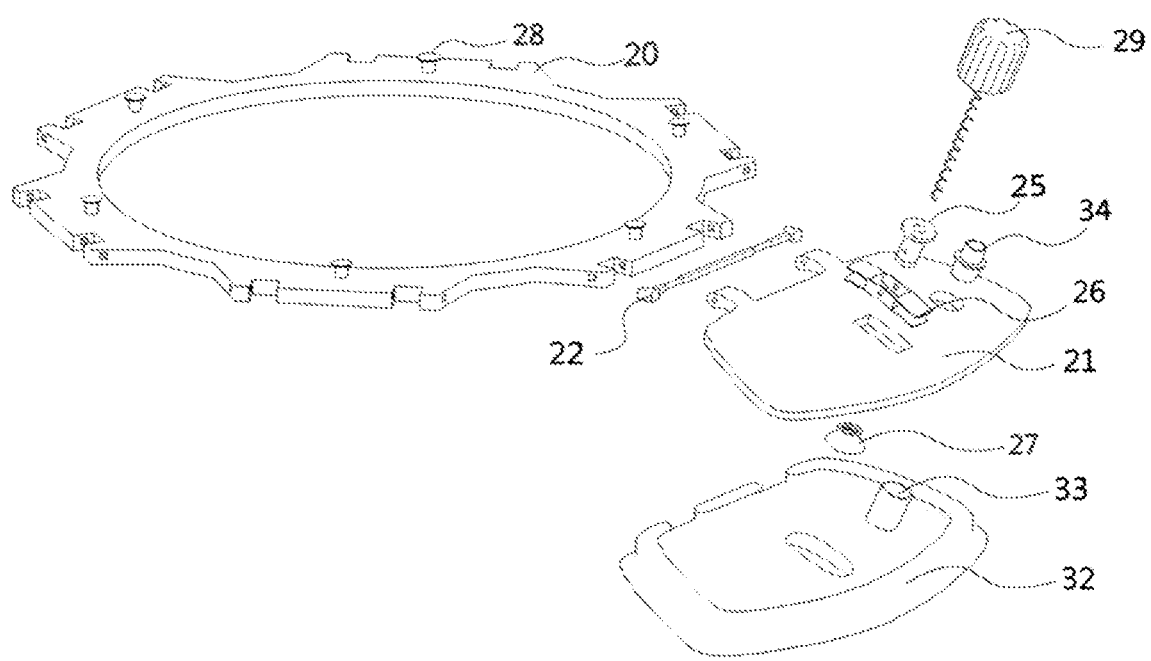
FIG. 2 is the integrated view of the fixation ring provided in the subject matter ventricular assist device together with the wing screws and wing nuts.
Figure 3:
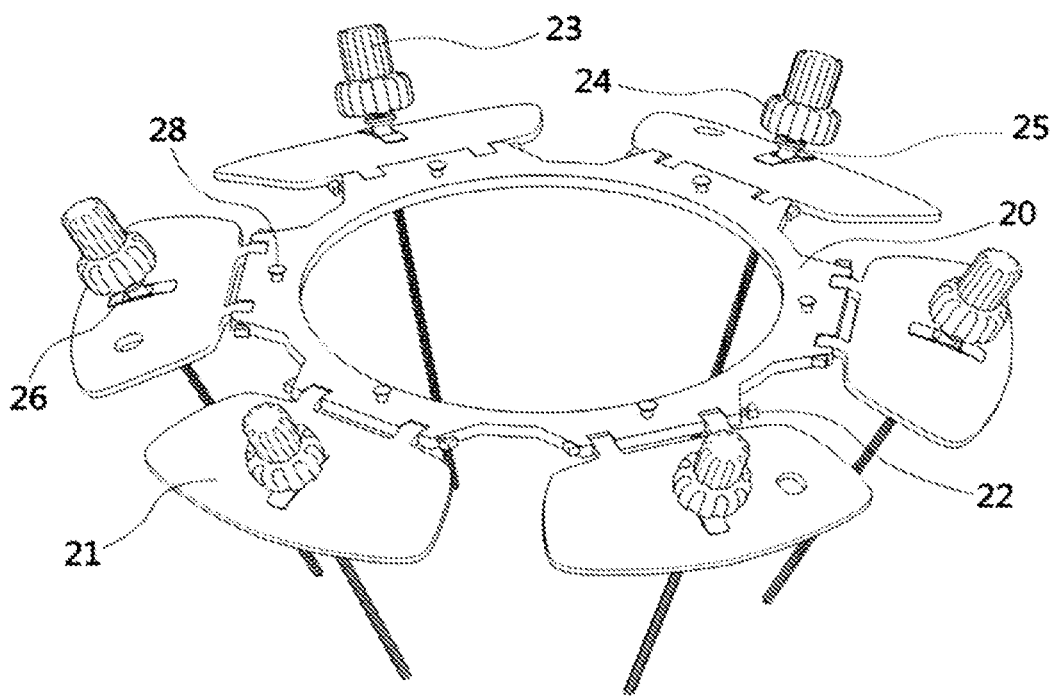
FIG. 3 is the view of the fixation ring parts and the silicon vacuum apparatus in the subject matter ventricular assist device.

As the engagement mechanism which provides fixation of the heart with the fixation ring (20), there is at least one fixation wing (21), at least one fixation wing shaft (22), at least one fixation wing screw (23), at least one fixation wing nut (24), at least one fixation wing screw positioner (25), at least one fixation wing screw positioner slider (26), at least one fixation pad (27), at least one fixation ring pin (28) and at least one temporary fixation screw (29). In FIG. 2 and FIG. 3, the view of the fixation ring (20) and the engagement mechanism is given.

Said fixation wing (21) provides fixation of the fixation ring (20) at the heart apex by means of vacuuming and screwing tools.

Said fixation wing shaft (22) provides the connection of the fixation wing (21) to the fixation ring (20). The fixation wing shaft (22) may exist at two separate positions where they are moved by pressing to the shaft heads, in the shaft housings thereof. In one of the positions thereof, the fixed wings are fixed at the determined positions and said fixed wings are used for alignment during screwing. In the other position, the one-axis movements of the wings are provided.

Said fixation wing screw (23) joins the inflow cannula (10) with the fixation ring (20) and provides fixation to the heart muscle.

Figure 7:
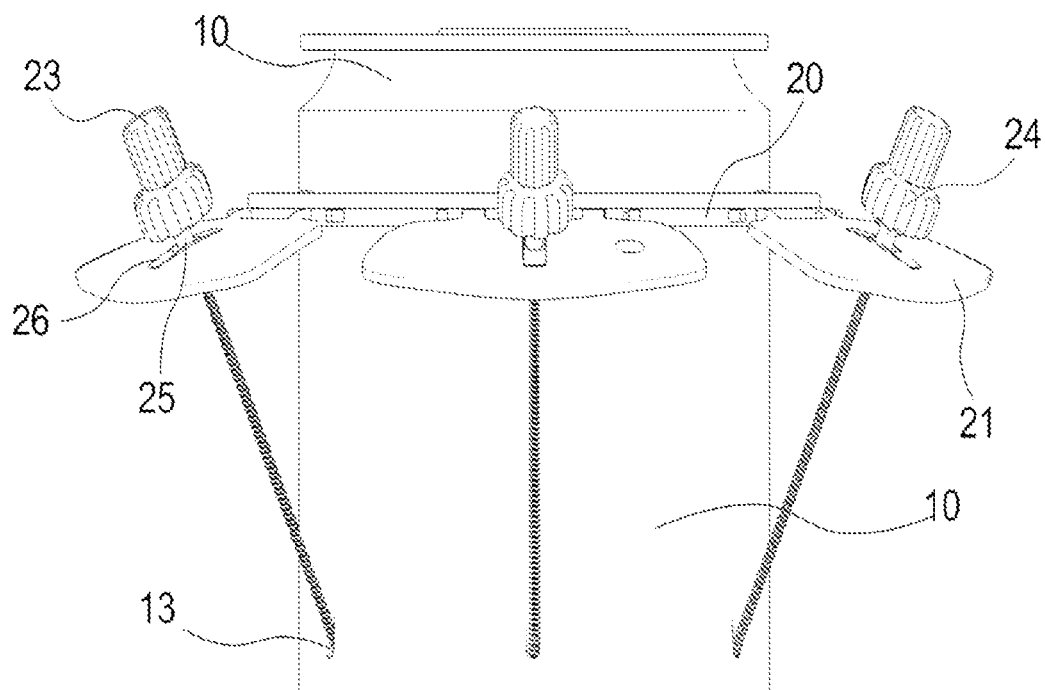
FIG. 7 is the frontal view where the inflow cannula and the fixation ring, provided in the subject matter ventricular assist device, are engaged with the wing screw and nuts.

As said fixation wing nut (24) is rotated in the clockwise direction as also shown in FIG. 7, the fixation wings (20) and thus the heart muscle are pushed towards the inflow cannula (10) and the inflow cannula (10) is fixed on the heart in a more stable manner as the gap around the inflow cannula (10) is covered.

Said fixation wing screw positioner (25) provides alignment of the fixation wing screws (23) with the wing screw housings (13) provided on the inflow cannula (10). Said alignment is possible at the position where all wing screw positioners are angled at maximum outwardly at the locked positions of the wings where said wing screw positioners are provided.

Said fixation wing screw positioner slider (26) is responsible for the movements of the fixation wing screw positioner (25) on the wings.

Said fixation pad (27) completely covers the inlet holes formed by the fixation wing screws (23) at the heart muscle and forms a barrier for bleeding. The fixation pad (27) is made of bio-compliant silicon.

Said fixation ring pin (28) is engaged with the fixation ring (20) pin housings provided on the inflow cannula (10) and provides locking of the inflow cannula (10) with the fixation ring (20).

Said temporary fixation screws (29) provide temporary fixation of the fixation wings (21), where the wing vacuum fixers (32) are fixed, to the heart muscle.

Figure 8:
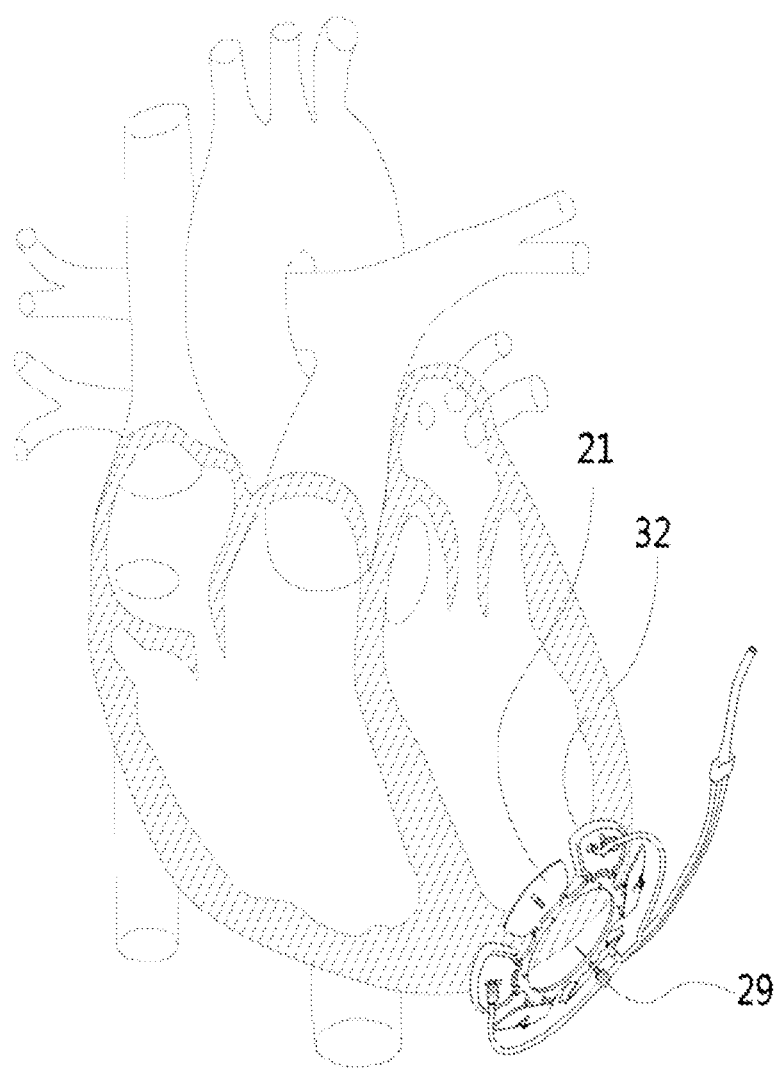
FIG. 8 is the view of the temporary fixation screws and the silicon vacuum wing fixer of the fixation ring, provided in the subject matter ventricular assist device, at the heart apex.

The subject matter ventricular assist device (1) comprises a vacuum fixer (30) as also shown in FIG. 8 and which provides vacuuming and fixation of the fixation ring (20), connected to said vacuum fixer (30), onto the heart surface. Said vacuum fixer (30) is made of bio-compliant silicon.

The vacuum fixer (30) is placed to the inner edge of the fixation ring (20) by means of tight-contact mechanism.

Figure 4:
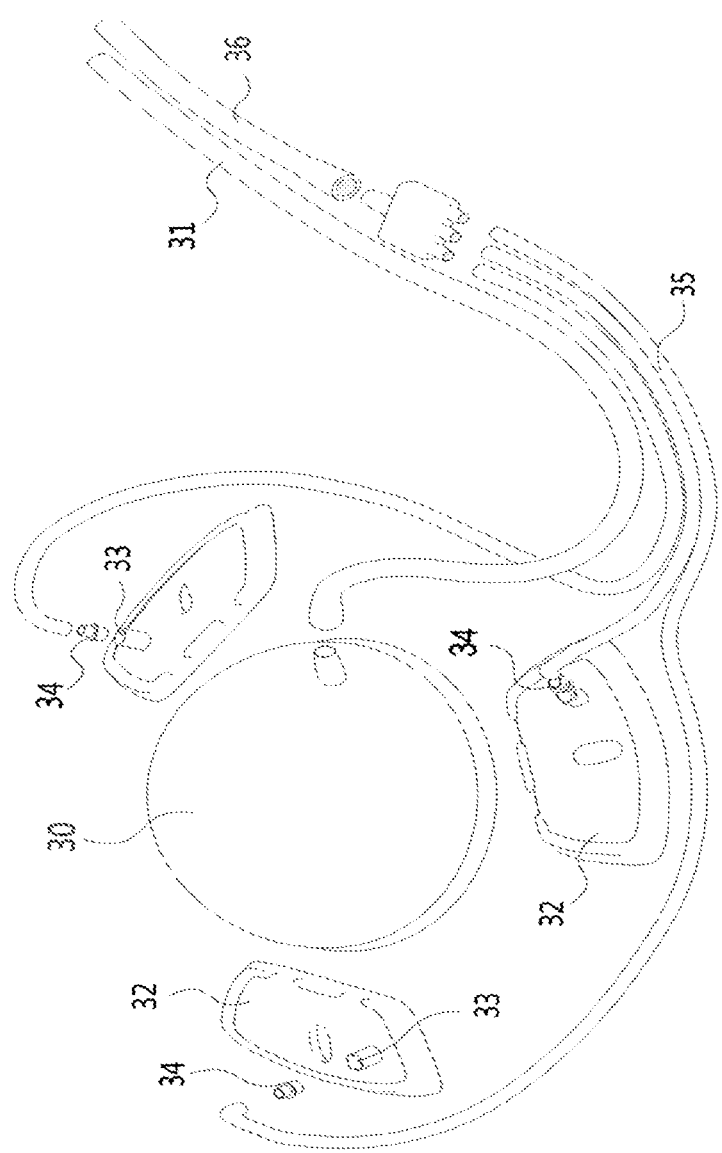
FIG. 4 is the view of the silicon vacuum apparatus and lines in the subject matter ventricular assist device.

As shown in FIG. 4, the vacuum fixer (30) comprises auxiliary mechanism elements in order to provide vacuuming process of the fixation ring (20), provided in the ventricular assist device as shown in FIG. 4, onto the heart surface. Said vacuum fixer (30) comprises a fixation ring vacuum tube (31), at least one wing vacuum fixer (32), at least one wing vacuum inlet (33), at least one wing vacuum connector (34), at least one wing vacuum tube (35) and at least one wing main vacuum tube (36).

Said fixation ring vacuum tube (31) provides the negative pressure to be transferred to the vacuum fixer (30). The fixation ring vacuum tube (31) is made of cylindrical and hollow bio-compliant silicon which has stiffness such that it does not become depressed as a result of negative pressure.

Said wing vacuum fixer (32) provides fixation of the fixation wings (20) on the heart surface. The wing vacuum fixer (32) is tightly held onto the heart surface by means of the negative pressure effect. The wing vacuum fixer (32) is made of bio-compliant silicon.

Said wing vacuum inlet (33) provides transfer of the negative pressure to the wing vacuum fixer (32).

Said wing vacuum connector (34) provides connection of the wing vacuum tubes to the wing vacuum inlets (33). The wing vacuum connector (34) is made of stiff, bio-compliant hollow plastic.

Said wing vacuum tube (35) provides transfer of the negative pressure to the wing vacuum fixers (32). The wing vacuum tube (35) is made of plastic pipe which has stiffness such that it does not become depressed as a result of negative pressure.

Said wing main vacuum tube (36) provides transfer of the negative pressure to the wing vacuum lines. The wing main vacuum tube (36) is made of bio-compliant silicon which has stiffness such that it does not become depressed as a result of negative pressure.

The subject matter ventricular assist device (1) comprises a core myocardium borer (40) which provides cutting of the heart muscle in a cylindrical manner from the heart apex and which provides removal of the core myocardium, and a core myocardium borer positioner (41) which holds the core myocardium borer (40) at a 90 degree axis to the inflow cannula (10) and which provides the heart muscle to be cut and removed at fixed position.

The subject matter ventricular assist device (1) essentially comprises a pump (50) which is connected to the ventricle in the heart and at least one pump shaft (51) engaged to the compressing windows provided in the inflow cannula (10) and which provides locking of the pump (50) with the inflow cannula (10).

Said pump (50) is produced modularly without inflow cannula. The design of the pump (50) provides placement of the most suitable inflow cannula (10) to the left ventricle of the patient by the surgeon.

By means of said pump pins (51), bleeding between the contact surfaces is prevented.

The present invention is moreover a cannula implantation method where surgical suture is not used and which provides implantation facilitation related to ventricular assist devices and which provides controlling of all bleeding sites.

In the present invention, the ventricular assist device (1), where the inflow cannula (10) is configured, is prepared for surgery by means of standard processes for the heart. The heart apex is marked with surgical marker pen for the selection of the area where the inflow cannula (10) is to be placed. The fixation ring (20) and the vacuum fixer (30) are contacted to the heart apex in a fixed manner such that the marked area stays at the center of the fixation ring (20) and negative pressure is applied to the vacuum fixer (30) apparatus. Said negative pressure value is 250 mmHg. Thanks to this, the fixation ring (20) is fixed to the heart apex by means of vacuum effect. Moreover, the fixation wings (21) are fixed to the heart muscle by means of wing vacuum fixers (32) with negative pressure. By means of vacuum effect, the fixation wings (21) on the heart surface are fixed to the heart muscle by means of temporary fixation screws (29).

Figure 9:
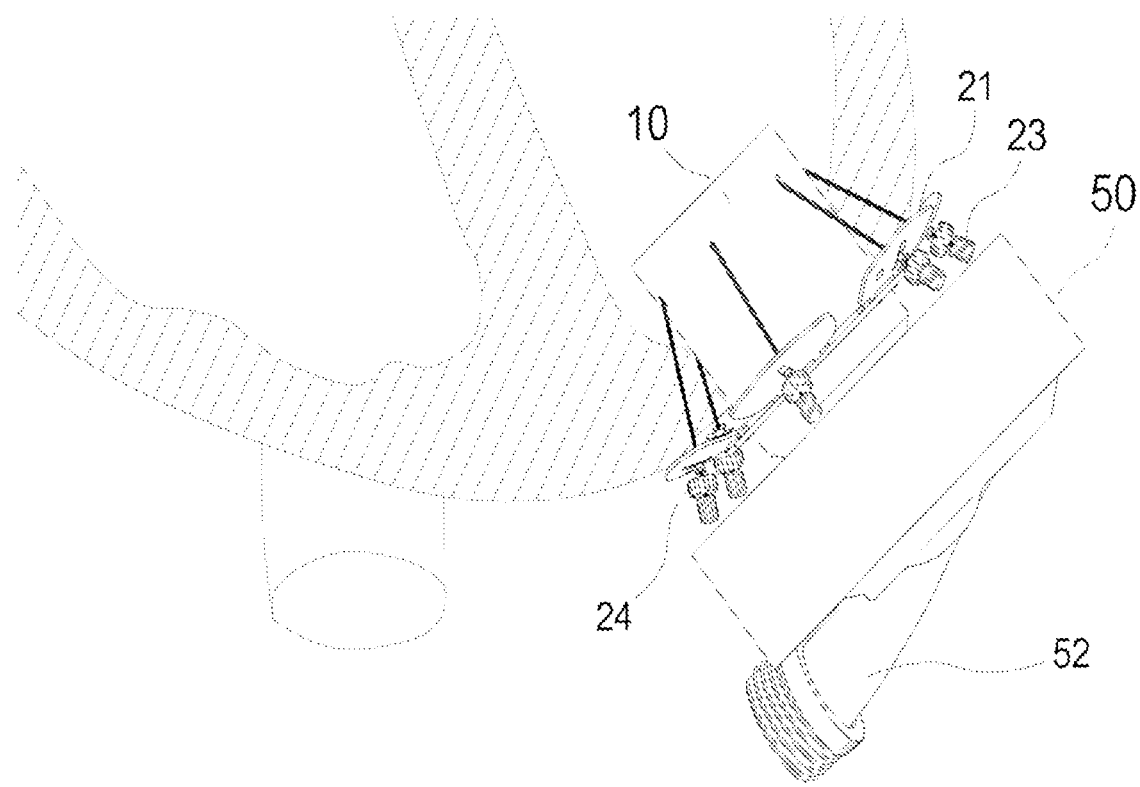
FIG. 9 is the view of the pump and outlet tube and the implantation to the heart with the nuts and the wing screws of the fixation ring and the inflow cannula.

As shown in FIG. 9, the surgeon can fix the fixation ring (20) to the heart surface in an easy and rapid manner by means of vacuum effect and by means of temporary fixation screws (29).

Figure 6:
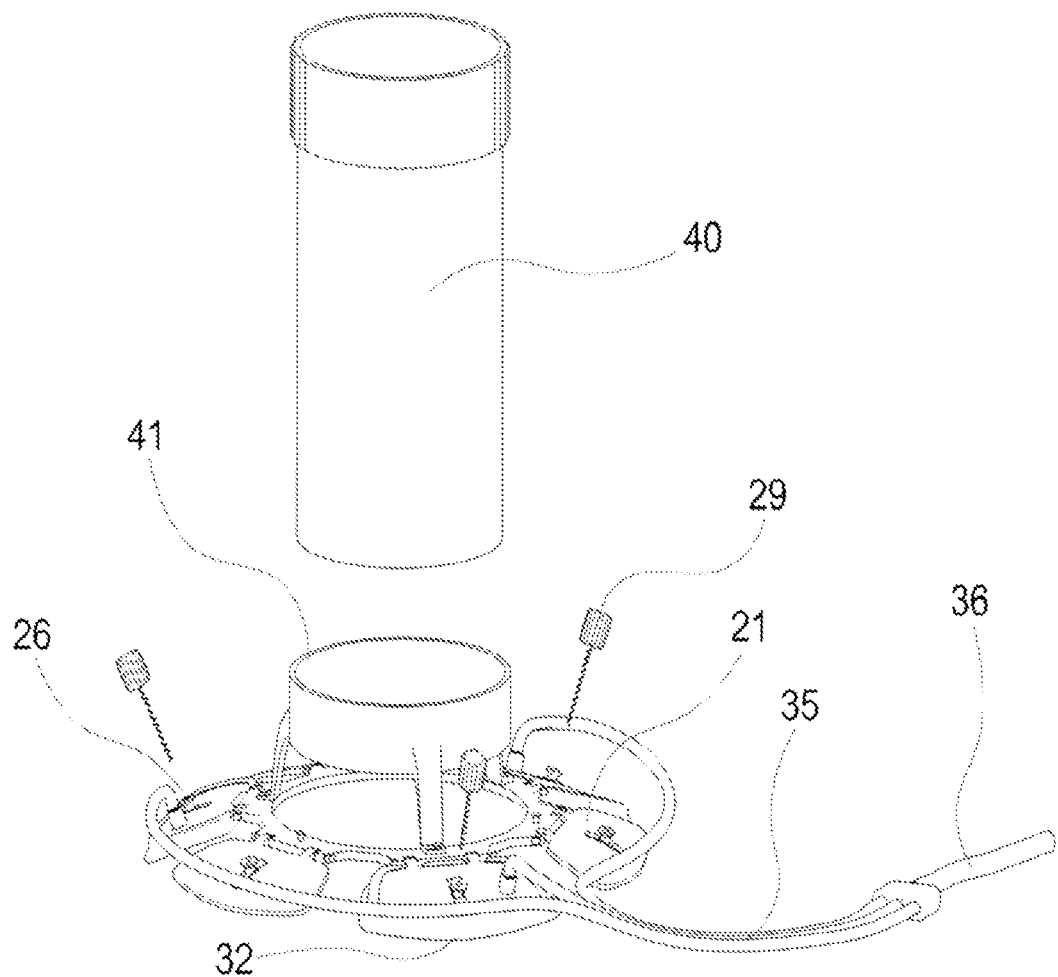
FIG. 6 is the view of the core myocardium borer and the positioner provided in the subject matter ventricular assist device.

Afterwards the vacuum fixer (30) is separated from the fixation ring (20). In this step, the fixation ring (20) is provided to stay fixed at the heart apex by means of the temporary fixation screws (29) and as a result of the negative pressure effect. The borer positioner (41) is engaged to the fixation ring pins (28) provided on the fixation ring (20) and is locked in the clockwise direction. The core myocardium borer (40) shown in FIG. 6 is passed through the borer positioner (41) and the marked heart muscle is cut in a cylindrical form and at an orthogonal position to the fixation ring (20). The core myocardium borer (40) and the borer positioner (41) are removed from the surgery medium, and afterwards, the cut heart core myocardium is removed.

From the inflow cannula (10) and the fixation ring (20) set designed in different sizes and formed in a compliant manner to the average heart sizes and left ventricle diameters for adult woman and man, the inflow cannula (10) which is sized in the most compliant manner to the left ventricle of the patient and the fixation ring (20) which is compliant to this cannula (10) are selected.

One of the improvements of the present invention is that inflow cannula (10) can be produced which is unique for the patient. Round sealed rubber ring (15), having suitable diameter, is engaged to the selected inflow cannula (10). The inflow cannula (10) is passed through the fixation ring and is advanced into the left ventricle. The fixation ring pins (28) are engaged to the fixation ring pin housings (11) provided on the inflow cannula (10). The inflow cannula (10) is rotated in the clockwise direction and is fixed when the fixation ring pins (28) are seated to the housings thereof.

In this step, the three fixation wing screws (23) are respectively passed through three fixed fixation wing screw positioners (25). In case the wing screw positioner sliders (26) are brought to the positions marked on the fixation wings (21), each fixation wing screw (23) is brought to the positioned where the angle is at maximum outwardly inside its own fixation wing screw positioner (25). This position means that the direction of the long axes of each fixation wing screw (23) is aligned with the wing screw housings (13) which are the correspondences thereof in the inflow cannula (10). Thus, the surgeon easily screws the fixation wing screws (23) to the wing screw housings (13) which stay in the heart and which cannot be seen from outside and the surgeon fixes the inflow cannula (10). Afterwards, the determined end of the fixation wing shafts (22) is pressed in the direction of the long axes thereof and the wing lock mechanism is opened. The fixation wing (20) is rotated in the clockwise direction and the three fixation wings (20) peripherally compress the heart muscle tissue towards the inflow cannula (10). This pressure provides filling of the peripheral space of the inflow cannula (10) with the heart muscle and provides obtaining a more stable inflow cannula (10). Moreover, the space around the inflow cannula (10), which may lead to a risk for bleeding control and for thrombus formation, is filled with heart muscle as much as possible.

The temporary fixation screws (29) of the movable fixation wings (21) are removed from the heart muscle and the negative pressure is eliminated and the wing vacuum fixers (32) are removed from the fixation wings (21). The fixation wings (21) peripherally compress the heart muscle towards the inflow cannula (10) with angles of 60 degrees.

In the final step, the flat sealed rubber ring (14) is placed to the rubber ring bed provided on the inflow cannula (10). The pump (50), designed according to the inflow cannula (10), is engaged to the pump pin housings (12), provided in the inflow cannula (10), by means of pump pins (51), and locking is provided by means of rotating in the clockwise direction. The engagement mechanisms of all inflow cannulas (10), provided at the set and which have different dimensions, with the pump (50) are standard.

The areas, where bleeding is theoretically probable, are the holes formed by the six fixation wing screws (23) in the heart muscle, the thin gap between the inflow cannula (10) and the fixation ring (20) and the thin layer gap between the inflow cannula (10) and the pump (50) contact surfaces. The probable blood leakage, which may occur through the regions where the fixation wing screws (23) enter to the heart muscle, has been taken under control by the bio-compliant fixation pads (27) provided on the fixation wing screw positioners (25). The round sealed rubber ring (15) has been placed as barrier for the probable blood leakage which may occur between the inflow cannula (10) and the fixation ring (20), and the flat sealed rubber ring (14) has been placed as barrier for the probable blood leakage which may occur through the thin layer between the inflow cannula (10) and the pump (50).

Since the steps of the procedure have been designed for every heart surgeon to realize application with the same algorithm and the same surgical manipulations, said procedure has been standardized. As a result, thanks to application facilitation and standardization of the procedure, surgical-focused gains are obtained and moreover, procedure duration and surgical complications are reduced and patient-focused healing will be obtained.

The protection scope of the present invention is set forth in the annexed claims and cannot be restricted to the illustrative disclosures given above, under the detailed description. It is because a person skilled in the relevant art can obviously produce similar embodiments under the light of the foregoing disclosures, without departing from the main principles of the present invention.

What is claimed is:

1. A ventricular assist device providing a sutureless implantation and an application facilitation and controlling of bleeding sites, comprising:
    an inflow cannula placed into a left ventricle, wherein the inflow cannula provides transferring of a blood, coming from the left ventricle, to a pump and the inflow cannula is made of a metal;
    a fixation ring locked to the inflow cannula, wherein the fixation ring provides fixation of the ventricular assist device at a heart apex;
    a vacuum fixer providing fixation by vacuuming the fixation ring, and connected to the fixation ring, by an effect of a negative pressure applied in the fixation ring;
    a core myocardium borer cutting a heart muscle in a cylindrical manner through the heart apex, wherein the core myocardium borer removes a core myocardium; and
    the pump-provides increasing an amount of the blood circulating in a body when the core myocardium borer and one of natural pumps do not operate properly,
    wherein the pump comprises at least one pump pin providing engagement to compressive windows provided at the inflow cannula and the at least one pump pin provides the pump to be locked to the inflow cannula.

2. The ventricular assist device according to claim 1, wherein the fixation ring comprises:
    at least one fixation wing as an engagement mechanism providing fixation of the fixation ring to a heart;
    the at least one fixation wing providing fixation of the fixation ring at the heart apex;
    at least one fixation wing shaft providing a connection of the at least one fixation wing to the fixation ring;
    at least one fixation wing screw joining the inflow cannula to the fixation ring, wherein the at least one fixation wing screw provides fixation of the inflow cannula to the heart muscle;
    at least one fixation wing nut providing the at least one fixation wing and the heart muscle to be pushed towards the inflow cannula by turning the at least one fixation wing nut clockwise and the at least one fixation wing nut fixes the inflow cannula on the heart by closing a gap around the inflow cannula;
    at least one fixation wing screw positioner providing an alignment with screw housings provided on the inflow cannula;
    at least one fixation wing screw positioner slider providing movements of the at least one fixation wing screw positioners on wings;
    at least one fixation pad completely covering inlet holes formed by the at least one fixation wing screws at the heart muscle, wherein the at least one fixation pad forms a barrier for bleeding;
    at least one fixation ring pin engaging with fixation ring pin housings provided on the inflow cannula, wherein the at least one fixation ring pin provides locking of the inflow cannula with the fixation ring; and
    at least one temporary fixation screw providing temporary fixation of the at least one fixation wing, wherein wing vacuum fixers are fixed, to the heart muscle.

3. The ventricular assist device according to claim 1, wherein the vacuum fixer comprises:
    a fixation ring vacuum tube providing transfer of the negative pressure to the vacuum fixer;
    at least one wing vacuum fixer providing fixation of fixation wings on a heart surface;
    a wing vacuum inlet providing transfer of the negative pressure to the at least one wing vacuum fixer (32);
    at least one wing vacuum connector providing connection of at least one wing vacuum tube to the wing vacuum inlet;
    the at least one wing vacuum tube providing transfer of the negative pressure to the at least one wing vacuum fixer; and
    a wing main vacuum tube providing transfer of the negative pressure to wing vacuum lines.

4. The ventricular assist device according to claim 3, wherein the fixation ring vacuum tube is made of a cylindrical and hollow bio-compliant silicon-having a stiffness providing the fixation ring vacuum tube to not become depressed as a result of the negative pressure.

5. The ventricular assist device according to claim 3, wherein the at least one wing vacuum fixer is made of a bio-compliant silicon.

6. The ventricular assist device according to claim 3, wherein the at least one wing vacuum connector is made of a stiff and bio-compliant hollow plastic.

7. The ventricular assist device according to claim 3, wherein the at least one wing vacuum tube is made of a plastic pipe having a stiffness providing the at least one wing vacuum tube to not become depressed as a result of the negative pressure.

8. The ventricular assist device according to claim 3, wherein the wing main vacuum tube is made of a bio-compliant silicon having a stiffness providing the wing main vacuum tube to not become depressed as a result of the negative pressure.

9. The ventricular assist device according to claim 1, wherein the core myocardium borer comprises a core myocardium borer positioner keeping the inflow cannula at an axis of 90 degrees and the core myocardium borer positioner provides the heart muscle to be cut and removed at a fixed position.

10. A ventricular assist device providing a sutureless implantation and an application facilitation and controlling of bleeding sites, comprising:
    an inflow cannula placed into a left ventricle, wherein the inflow cannula provides transferring of a blood, coming from the left ventricle, to a pump and the inflow cannula is made of a metal;
    a fixation ring locked to the inflow cannula, wherein the fixation ring provides fixation of the ventricular assist device at a heart apex;
    a vacuum fixer providing fixation by vacuuming the fixation ring, and connected to the fixation ring, by an effect of a negative pressure applied in the fixation ring;

a core myocardium borer cutting a heart muscle in a cylindrical manner through the heart apex, wherein the core myocardium borer removes a core myocardium; and the pump-provides increasing an amount of the blood circulating in a body when the core myocardium borer and one of natural pumps do not operate properly, wherein the inflow cannula comprises:
- at least one fixation ring pin housing engaged with fixation ring pins, wherein the at least one fixation ring pin housing provides a locking of the pump and the inflow cannula;
- at least one pump pin housing engaged to pump pins, wherein the at least one pump pin housing provides the locking of the pump and the inflow cannula;
- at least one fixation wing screw housing providing fixation of fixation wing screws to the inflow cannula;
- at least one flat sealed rubber ring filling a thin layer gap between contact surfaces of the pump and the inflow cannula, wherein the at least one flat sealed rubber ring prevents a probable blood leakage through the thin layer gap; and
- a round sealed rubber ring filling a thin layer gap between contact surfaces of the fixation ring and the inflow cannula, wherein the round sealed rubber ring prevents the probable blood leakage through the thin layer gap.

11. The ventricular assist device according to claim 10, wherein the at least one flat sealed rubber ring is made of a bio-compliant silicon material.

12. The ventricular assist device according to claim 10, wherein the round sealed rubber ring is made of a bio-compliant silicon material.

* * * * *